United States Patent
Dansereau et al.

[11] Patent Number: 5,381,699
[45] Date of Patent: Jan. 17, 1995

[54] RADON COLLECTOR AND BUBBLER

[75] Inventors: Robert E. Dansereau, Albany, N.Y.; Joseph A. Hutchinson, Henderson, Nev.

[73] Assignee: Health Research, Inc., Albany, N.Y.

[21] Appl. No.: 958,047

[22] Filed: Oct. 6, 1992

[51] Int. Cl.⁶ .................. G01N 1/02; G01N 33/18; B01L 3/02
[52] U.S. Cl. .................. 73/864.01; 73/863.23; 73/864.13; 73/864.24; 73/864.81
[58] Field of Search .......... 73/863.21, 863.23, 864.01, 73/864.11, 864.13, 864.15, 864.16, 864.21, 864.24, 864.81, 864.87

[56] References Cited

U.S. PATENT DOCUMENTS

| | | | |
|---|---|---|---|
| 4,256,461 | 3/1981 | Wallace | 23/230 B |
| 4,301,117 | 11/1981 | Smernoff | 422/99 |
| 4,895,808 | 1/1990 | Romer | 73/863.21 |
| 4,912,323 | 3/1990 | Bhat et al. | 250/252.1 |
| 4,973,450 | 11/1990 | Schlüter | 73/863.23 |
| 5,006,240 | 4/1991 | Stefero, Sr. | 210/223 |
| 5,045,215 | 9/1991 | Lamarre | 210/747 |
| 5,047,634 | 9/1991 | Guelin et al. | 250/255 |
| 5,055,674 | 10/1991 | Kotrappa | 250/255 |
| 5,110,558 | 5/1992 | Romer | 73/863.21 |

FOREIGN PATENT DOCUMENTS

| | | | |
|---|---|---|---|
| 75975 | 6/1976 | Australia | 73/863.23 |
| 1209778 | 1/1966 | Germany | 73/864.16 |
| 79430 | 5/1982 | Japan | 73/863.21 |
| 1573377 | 6/1990 | U.S.S.R. | 73/863.23 |

OTHER PUBLICATIONS

Axelrod et al., "New Bubbler Design for Atmosphere Sampling", Analytical Chemistry, vol. 43, No. 13, pp. 1916–1917, Nov. 1971.
Berg et al., "First Measurements of Total Chlorine and Bromine in the Lower Stratosphere", Geophysical Research Letters, vol. 7, No. 11, pp. 937–940, Nov. 1980.
Shklovskii, "Moderization of Msh-10 Microsyringe", Ind. Lab (USA), vol. 16, No. 8, p. 1173, Aug. 1975.

*Primary Examiner*—Hezron E. Williams
*Assistant Examiner*—Daniel S. Larkin
*Attorney, Agent, or Firm*—Heslin & Rothenberg

[57] ABSTRACT

The radon collector and bubbler includes a syringe having a hollow barrel with an outlet means at its end and a hollow plunger defining a chamber therein which is insertable within the hollow barrel and axially slidable therein. The hollow plunger has a means for dispersing air within the hollow barrel and a means for sealing the area between the syringe and hollow plunger. A hollow tube is located within the hollow plunger and contains charcoal therein. An inlet means is connected to the hollow tube and places the hollow tube in air flow relationship with an area outside the hollow plunger and syringe. During operation, a liquid to be sampled is suctioned into the syringe through the outlet means. Air is then drawn via the inlet means into the hollow barrel of the syringe and the radon therein is absorbed onto the charcoal within the hollow tube. Air flowing within the hollow tube is dispersed so that it will collect radon from the water to be tested.

12 Claims, 1 Drawing Sheet

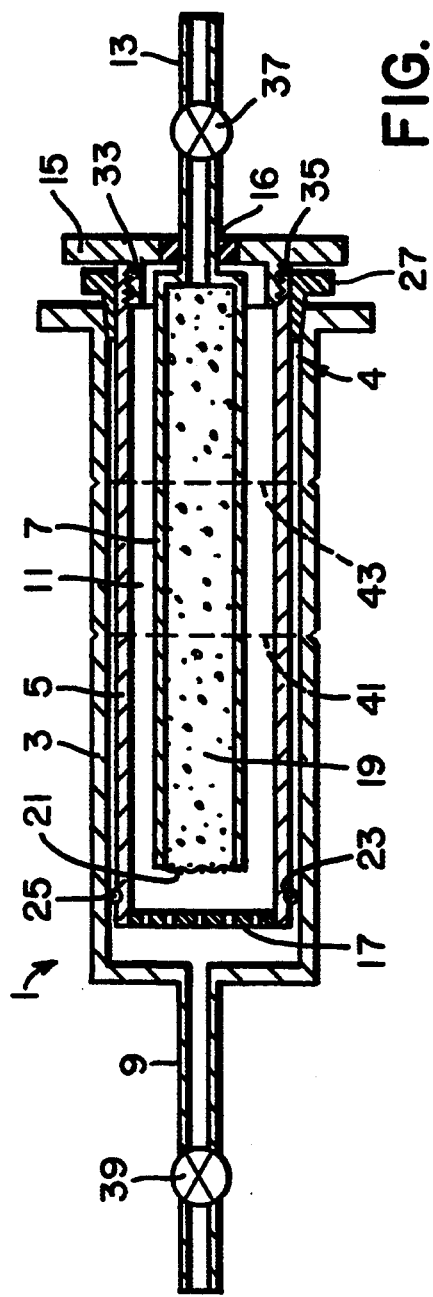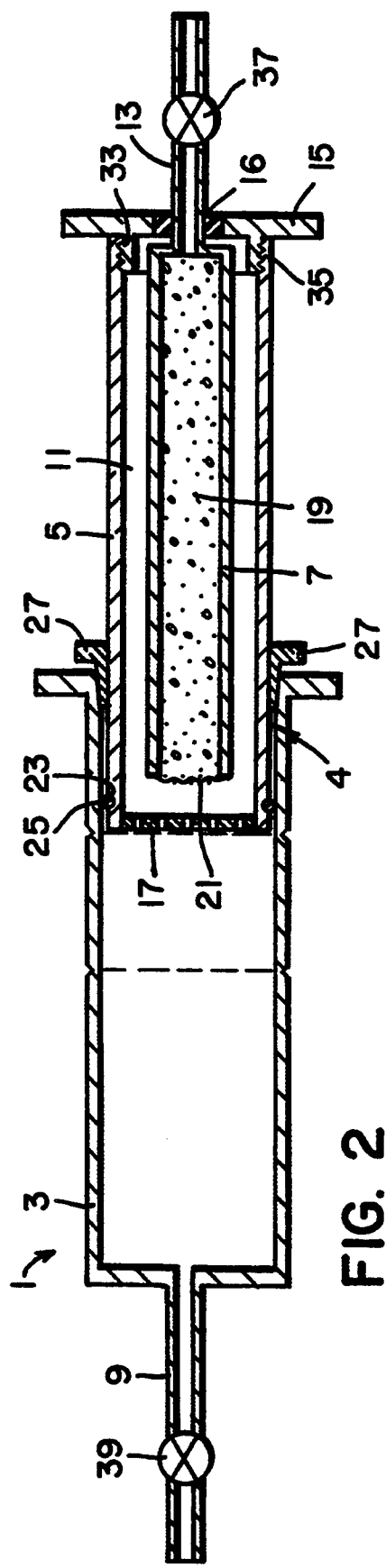

5,381,699

RADON COLLECTOR AND BUBBLER

BACKGROUND OF THE INVENTION

This invention relates to the field of radon testing and in particular, to a radon collector and bubbler.

The effects of radon are known to be detrimental to the human body. Recently, it has been found that high levels of radon gas have been detected in various homes. Although the radon usually emits from the earth, water supplies have also been known to contain relatively high levels of radon therein which may be released and enter into the air. Currently, there are no drinking water regulations relating to a maximum contaminant level of radon. However, proposed federal drinking water regulations establish a maximum contaminant level of 300 pCi/l for radon. These proposed regulations, however, are applicable only to public water supplies and not to private water supply systems.

Currently available analytical techniques are capable of measuring radon concentration levels, but field measurement techiques have a high level of uncertainty. The Lucas cell method and liquid scintillation methods are commonly used to measure radon levels in water. The liquid scintillation method requires a liquid scintillation spectrometer which is only present within a laboratory. Field measurements using this technique are impractical. The Lucas cell method requires the transfer of sample water using fragile equipment. The transfer and transport of sample water allows for radon loss possibly causing inaccurate test results. Moreover, when a water sample is collected for transport to a laboratory, the container must be completely filled with the sample so as to prevent any radon gas from escaping therefrom. If the container is not completely filled, radon loss will occur, causing an inaccurately low concentration level result.

It is therefore an object of the present invention to provide a radon collector and bubbler which is capable of being used in the field.

It is also an object of the present invention to provide a radon collector and bubbler which prevents the exposure of sample liquid such as water to airborne radon.

It is also an object of the present invention to provide a radon collector and bubbler which does not require the sample liquid such as water to be transferred prior to measurement by a Lucas cell.

SUMMARY OF THE INVENTION

The aforementioned objects and advantages are achieved by a radon collector and bubbler constructed in accordance with the principles of the present invention. The radon collector and bubbler includes a syringe having a hollow barrel with an outlet means at end thereof, a hollow plunger defining a chamber therein which is insertable within the hollow barrel of the syringe and is axially slidable therein. The hollow plunger may have a means for dispersing air within the hollow barrel, a hollow tube located within the hollow plunger, means for sealing an area between the syringe and hollow plunger, means for retaining charcoal within the tube and for allowing air to pass through the tube, an inlet means for placing a hollow tube in air flow relationship with an area outside the hollow plunger and syringe.

The hollow tube is filled with charcoal. An outlet means may include an outlet stopcock and an inlet means may include an inlet stopcock. The means for preventing a hollow plunger from retracting into the hollow barrel of the syringe may also be included. The means for preventing the hollow plunger from retracting into the barrel may include a clamp. A removable end cap may be threaded to the hollow plunger for allowing insertion of the hollow tube within the chamber of the hollow plunger. The means for sealing the area between the hollow plunger and the syringe may be an O-ring. The means for dispersing air may be a fritted disk located at an end of the hollow plunger within the barrel.

BRIEF DESCRIPTION OF THE DRAWINGS

FIG. 1 depicts a sectional view from the side of a radon collector and bubbler having the hollow plunger in a retracted position constructed in accordance with principles of the present invention; and FIG. 2 depicts a sectional view from the side of the radon collector and bubbler shown in FIG. 1 having the hollow plunger in an extended position.

DETAILED DESCRIPTION

Referring to FIG. 1, the collector and bubbler includes a syringe 1 and a hollow plunger 5 axially slidable therein. A hollow tube 7 is located within the hollow plunger. The syringe 1 has a hollow inner portion or barrel 3 with an outlet means 9 located at one end thereof. The opposite end contains an opening 4. A hollow plunger 5 is inserted into the opening 4 and mounted within the hollow barrel 3 of the syringe 1 so as to be axially slidable therein. The hollow plunger 5 contains a chamber 11 therein. A hollow tube 7 is axially inserted within the chamber 11 of the hollow plunger 5. The hollow tube 7 contains an inlet 13 at one axial end thereof. Preferably, the hollow tube 7 extends from the axial end disposed opposite the outlet means 9. The inlet 13 extends through an end cap 15 of the hollow plunger 5.

A fritted disk 17 is located at the end of the hollow plunger 5 inserted within the hollow barrel 3 of the syringe 1. The fritted disk 17 acts as a means for dispersing gases, such as air, therethrough into the hollow barrel 3 to sparge a liquid, typically water, within the barrel 3. Other means for dispersing a gas such as air and sparging the liquid may be used in lieu of the fritted disk 17. The fritted disk 17 is press fit into a hole located at the end of the hollow plunger inserted into the hollow barrel 3 of the syringe 1. However, other means for securing the fritted disk 17 may also be used.

The hollow tube 7 contains charcoal 19 therein. Located at the end of the hollow tube 7 inserted within the chamber 11 of the hollow plunger 5 (located at the opposite end of the tube 7 having the inlet 13 connected thereto) is a means for retaining the charcoal 19 within the hollow tube 7. The means must also allow a gas such as air to pass through the hollow tube. This means may include, but is not limited to, a sieve retainer 21.

The hollow plunger 5 may contain a groove 23 located at the same axial end thereof as the fritted disk 17. The groove may contain an O-ring 25 therein for sealing the area between the hollow plunger 5 and hollow barrel 3 of the syringe 1. However, other means for sealing the area between the hollow plunger 5 and the syringe 1 may also be used. A clamp 27 acting as means for preventing the hollow plunger 5 to retract past a certain position relative to the syringe 1 may be affixed to the hollow plunger 5. The clamp 27 is typically shaped as a collar which locks onto the plunger 5. When the clamp 27 contacts the syringe 1, the plunger cannot slide and retract further into the barrel 3 of the syringe 1. Although a clamp 27 is preferred, other means for locking the hollow plunger into a fixed position may suffice. The hollow plunger 5 may have an end cap 15 at the axial end thereof opposite the fritted disk 17. The end cap 15 may contain a threaded section 33 which fits a complimentary threaded section 35 of the hollow plunger 5 so as to be affixed thereto. The end cap 15 contains an aperture 16 therein at its face. The inlet means 13 of the hollow tube 7 extends through the aperture 16. Preferably, the inlet means 13 is press fit into the aperture so as to form an air tight seal. However, other means for sealing the outlet means from the chamber 11 of the hollow plunger 5 will suffice. The inlet means 13 contains an inlet stopcock 37 while the outlet means 9 contains an outlet stopcock 39. The outlet stopcock 39 enables the hollow barrel 3 to be in air flow relationship with the outlet means 9 and the inlet stopcock 37 allows air to flow into the hollow tube 7.

For convenience, the syringe may have graduation marks 41, 43 imprinted thereon to specify the volume within the hollow barrel 3 when the hollow plunger 5 is extended to a position where the O-ring 25 coincides with a particular graduation. Preferably, a 15 milliliter graduation mark 41 and a 20 milliliter graduation mark 43 are located on the plunger.

Operation of the radon collector and bubbler will now be described. Initially, the hollow plunger 5 is in a fully depressed position as shown in FIG. 1. The outlet stopcock 39 is opened and the inlet stopcock 37 is closed. The outlet means 9 is placed such that the end cap 15 is located above the outlet means 9 into a liquid, such as water, to be tested for radon concentration levels. To draw water into the hollow barrel 3 of the syringe 1 the plunger is withdrawn so that the O-ring 25 coincides with the first graduation marker 41. In this case, fifteen milliliters of water are drawn through the outlet means 9 and into the hollow barrel 3 of the syringe 1. At this position, the hollow plunger 5 is in an extended position. With the plunger extended, the outlet stopcock 39 is closed and the inlet stopcock 37 is opened. The syringe 1 is now inverted so that the outlet means 9 is located above the inlet 13. The hollow plunger 5 is withdrawn further, preferably to the second graduation so 43 that 5 milliliters of air flows into the inlet means 13. The inlet air flows through the inlet stopcock 37 through the hollow tube 7 passing through the charcoal 19 therein which absorbs any radon within the air. The radon-free air which exits the hollow tube 7 through the sieve retainer 21 passes through the fritted disk 17 causing sparging the liquid sample within the hollow barrel 3 to cause dissolved radon to rise to the top of the hollow barrel 3. A clamp 27 is now locked so that the hollow plunger 5 cannot be moved. At this time, the hollow barrel 3 contains 15 milliliters of liquid, water and 5 milliliters of air.

At this time, the collector and bubbler may be attached to an evacuated Lucas cell device, which is well known in the art. The outlet means 9 is connected to the inlet of the Lucas device and the inlet stopcock 37 opened so that air is drawn through the inlet means 13, through the hollow tube 7 and fritted disk 17. The liquid within the barrel 3 is sparged by the air and any radon from the water within the hollow barrel 3 will rise and pass through the outlet means 9. The radon level within the outlet air is then measured by the Lucas cell device to arrive at a radon concentration level for the liquid (water) which was sampled.

Although the invention has been described in connection with the embodiment depicted herein, it will be apparent to one skilled in the art that various modifications and changes may be made to this embodiment without departing in any way from the spirit of the invention as defined by the following claims.

What is claimed:

1. A radon collector and bubbler comprising:
   a syringe defining a hollow barrel with an outlet means at an end thereof;
   a hollow plunger defining a chamber therein, said hollow plunger being insertable within the hollow barrel and being axially slidable therein, said hollow plunger having a means for dispersing air into the hollow barrel;
   a hollow tube located within the hollow plunger;
   means for sealing an area between the syringe and the hollow plunger;
   means for retaining charcoal within the tube and for allowing air to pass through the tube;
   an inlet means for placing the hollow tube in air flow relationship with an area outside the hollow plunger and syringe.

2. The radon collector and bubbler of claim 1 wherein the hollow tube is filled with charcoal.

3. The radon collector and bubbler of claim 2 wherein the outlet means comprises an outlet stopcock.

4. The radon collector and bubbler of claim 3 wherein the inlet means comprises an inlet stopcock.

5. The radon collector and bubbler of claim 4 further comprising a means for preventing the hollow plunger from retracting into the barrel of the syringe.

6. The radon collector and bubbler of claim 5 further comprising a removable end cap thereof, said removable end cap capable of being threaded to the hollow plunger and for allowing insertion of the hollow tube within the chamber of the hollow plunger.

7. The radon collector and bubbler of claim 5 wherein the means for preventing the hollow plunger from retracting into the barrel comprises a clamp.

8. The radon collector and bubbler of claim 1 or 5 wherein the means for sealing the area between the hollow plunger and the syringe comprises an 0-ring.

9. The radon collector and bubbler of claim 1 wherein the means for dispersing air comprises a fritted disk located at an end of the hollow plunger within the barrel.

10. A method of collecting radon contaminated water to be tested for radon levels therein comprising:
    inserting an outlet means at an end of a syringe defining a hollow barrel into a water sample, said syringe comprising a hollow plunger being insertable within the hollow barrel and being axially slidable therein and having a means for dispersing air into the hollow barrel, a hollow tube located within the hollow plunger, means for sealing an area between the syringe and the hollow plunger, means for retaining charcoal within the tube and for allowing air to pass through the tube, and an inlet means for placing the hollow tube in air flow relationship with an area outside the hollow plunger and syringe;
    withdrawing said hollow plunger to collect said water within said hollow barrel with said outlet means opened and said inlet means closed;

opening said inlet means and closing said outlet means;

further withdrawing said hollow plunger to allow air through the inlet; and closing said inlet means.

11. The method of claim 10 further comprising locking said hollow plunger into position.

12. The method of claim 11 further comprising attaching said outlet means to a Lucas cell device.

* * * * *